(12) United States Patent
Matsuda et al.

(10) Patent No.: US 7,704,917 B2
(45) Date of Patent: Apr. 27, 2010

(54) PROCESS FOR PRODUCING CATALYST FOR CYANHYDRIN HYDRATION AND PRODUCT OF THE PROCESS

(75) Inventors: Hideho Matsuda, Tokyo (JP); Takako Uchiyama, Niigata (JP); Yoshikazu Shima, Niigata (JP); Masaki Takemoto, Niigata (JP)

(73) Assignee: Mitsubishi Gas Chemical Company, Inc., Chiyoda-Ku, Tokyo (JP)

( * ) Notice: Subject to any disclaimer, the term of this patent is extended or adjusted under 35 U.S.C. 154(b) by 100 days.

(21) Appl. No.: 11/994,629

(22) PCT Filed: Jul. 6, 2006

(86) PCT No.: PCT/JP2006/313479

§ 371 (c)(1),
(2), (4) Date: Jan. 3, 2008

(87) PCT Pub. No.: WO2007/007633

PCT Pub. Date: Jan. 18, 2007

(65) Prior Publication Data

US 2009/0036301 A1  Feb. 5, 2009

(30) Foreign Application Priority Data

Jul. 8, 2005  (JP)  ............... 2005-200591

(51) Int. Cl.
*B01J 23/32* (2006.01)
*C01G 45/12* (2006.01)
*C07C 231/00* (2006.01)

(52) U.S. Cl. .................. 502/324; 423/599; 564/126
(58) Field of Classification Search ............... None
See application file for complete search history.

(56) References Cited

U.S. PATENT DOCUMENTS 4,987,256 A * 1/1991 Ebata et al. ............... 564/126

FOREIGN PATENT DOCUMENTS

| EP | 0956898 A2 | 11/1999 |
|---|---|---|
| JP | H03-068447 A | 3/1991 |
| JP | H03-093761 A | 4/1991 |
| JP | H05-170720 A | 7/1993 |
| JP | H06-269666 A | 9/1994 |
| JP | H07-076563 A | 3/1995 |
| JP | H09-019637 A | 1/1997 |
| JP | H09-024275 A | 1/1997 |
| JP | H11-319558 A | 11/1999 |

* cited by examiner

*Primary Examiner*—Melvin C Mayes
*Assistant Examiner*—Sarah Van Oudenaren
(74) *Attorney, Agent, or Firm*—Fitch, Even, Tabin & Flannery

(57) ABSTRACT

A process for producing a catalyst for cyanhydrin hydration, which comprises a manganese oxide as a main component and is excellent in both physical strength and reaction activity, is provided, as well as a catalyst for cyanhydrin hydration obtained by the production process. Specifically, a process for producing a catalyst which is useful for cyanhydrin hydration and contains a manganese oxide as a main component, potassium, and one or more elements selected from the group consisting of bismuth, vanadium and tin, in which the above compounds are mixed together in an aqueous system; the resulting slurry precipitate is subjected to solid-liquid separation; and the resulting hydrous cake is dried in at least two separate stages comprising a predrying and a main drying, is provided, as well as a catalyst for cyanhydrin hydration obtained by the production process.

10 Claims, No Drawings

PROCESS FOR PRODUCING CATALYST FOR CYANHYDRIN HYDRATION AND PRODUCT OF THE PROCESS

This Application is U.S. National Stage Application under 35 U.S.C. 371 of International Application PCT/JP2006/313479 filed Jul. 6, 2006, which designated the United States but was not published in English, and further claims the benefit from Japanese patent application number 2005-200591 Jul. 8, 2005, the complete disclosures of which are incorporated herein by reference.

TECHNICAL FIELD

The present invention relates to a process for producing a catalyst used for hydration reaction of cyanhydrins, the catalyst comprising a manganese oxide as a main component and being excellent in both physical strength and reaction activity, and a catalyst for cyanhydrin hydration obtained by the production process. For example, hydroxycarboxylic acid amide obtained by hydrating acetone cyanhydrin, one of the cyanhydrins, is a compound important as a raw material for producing hydroxycarboxylic acid esters or unsaturated carboxylic acid esters, and accordingly, development of a catalyst for cyanhydrin hydration with excellent performance for these purposes has a great significance in industry.

BACKGROUND ART

As catalysts that are useful for cyanhydrin hydration and exhibit high activity and high selectivity, various catalysts composed mainly of manganese oxides have been disclosed together with production processes for such catalysts (see, for example, Patent Documents 1 to 8). However, these catalysts are still problematic in that when they are used industrially, their structures are insufficient in physical strength, and hence collapse or pulverization of the catalysts are caused, inevitably resulting in increase of pressure loss and concomitant degradation of productivity so as to disturb continuation of operation.

Patent Document 1: Japanese Patent Laid-Open No. 63-57534
Patent Document 2: Japanese Patent Laid-Open No. 63-57535
Patent Document 3: Japanese Patent Laid-Open No. 3-68447
Patent Document 4: Japanese Patent Laid-Open No. 3-93761
Patent Document 5: Japanese Patent Laid-Open No. 5-170720
Patent Document 6: Japanese Patent Laid-Open No. 6-269666
Patent Document 7: Japanese Patent Laid-Open No. 9-19637
Patent Document 8: Japanese Patent Laid-Open No. 9

DISCLOSURE OF THE INVENTION

Problems to be Solved by the Invention

An object of the present invention is to provide a process for producing a catalyst for cyanhydrin hydration that solves the above-described problems in conventional techniques, namely, a catalyst that contains a manganese oxide as a main component and is industrially useful and advantageous with high activity and high selectivity as well as excellent strength.

Means for Solving the Problems

The present inventors made a diligent investigation in order to solve the above-described problems, and consequently made the present invention by finding out that physical strength of the catalyst for cyanhydrin hydration can be improved without impairing the reaction activity of the catalyst in the following way: specific compounds are mixed together in an aqueous system; a slurry of the resultant precipitates is subjected to solid-liquid separation; and the resultant hydrous cake is dried by a drying method in which a predrying is carried out under specific conditions, and thereafter a main drying is carried out.

Specifically, as described in the following items (1) to (7), the present invention relates to a process for producing a catalyst that is useful for cyanhydrin hydration and contains a manganese oxide as a main component with excellent physical strength and reaction activity, and also relates to a catalyst for cyanhydrin hydration, which is obtained by the production process.

(1) A process for producing a catalyst for cyanhydrin hydration, the catalyst comprising a manganese oxide as a main component, potassium, and one or more elements selected from the group consisting of bismuth, vanadium and tin, which comprises mixing the above compounds together in an aqueous system; subjecting the resulting precipitate in a form of slurry to solid-liquid separation; and drying the resulting hydrous cake in at least two separate stages comprising a predrying and a main drying.

(2) The process for producing a catalyst for cyanhydrin hydration, according to the above item (1), wherein the predrying is carried out at a drying temperature of 20 to 50° C. and at an average drying rate of 2 to 10 wt %/hr (based on dry weight) until water content of the hydrous cake reaches 100 wt % (based on dry weight) at the maximum.

(3) The process for producing a catalyst for cyanhydrin hydration, according the above item (1), wherein the main drying is carried out at a drying temperature of 100 to 200° C. until water content of the hydrous cake reaches 15 wt % (based on dry weight) at the maximum.

(4) The process for producing a catalyst for cyanhydrin hydration, according to any one of the above items (1) to (3), wherein the catalyst for cyanhydrin hydration is a composite oxide represented by the following formula (I):

$$Mn_aK_bBi_cO_d \qquad (1)$$

wherein with the proviso of a=1, b is 0.005 to 0.15, c is 0.001 to 0.1, and d is an atomic ratio of oxygen required for satisfying the valencies of the above-described respective elements.

(5) The process for producing a catalyst for cyanhydrin hydration, according to the above item (4), wherein the bismuth compound used in preparation of the catalyst is bismuth oxide.

(6) A catalyst for cyanhydrin hydration, produced by the process according to any one of the above items (1) to (5).

(7) The catalyst for cyanhydrin hydration, according to (6), which has a macropore distribution the maximum value of which falls in a range of 400 Å or more in terms of pore diameter.

EFFECTS OF THE INVENTION

According to the present invention, a catalyst for cyanhydrin hydration is provided, which has a high activity and a long life and is excellent in strength. Use of this catalyst enables, for example, a long term and stable production of hydroxycarboxylic acid amide from acetone dyanhydrin, and this is of great significance in industry.

BEST MODE FOR CARRYING OUT THE INVENTION

Hereinafter, the embodiment of the present invention is described in detail. In the present catalyst for cyanhydrin hydration which contains a manganese oxide as a main component, potassium and one or more elements selected from the group consisting of bismuth, vanadium and tin, the manganese dioxide as the main component is a manganese oxide falling between $MnO_{1.7}$ and $MnO_2$ in general. As the crystal structure of manganese dioxide, $\alpha$, $\beta$, $\gamma$, $\delta$, $\epsilon$ and the like are known. However, the structure is extremely complicated and of great variety, since there occur transitions between respective phases and changes in crystallinity degree.

Manganese dioxide exists in nature. However, when manganese dioxide is used as a catalyst, preferably used is manganese dioxide prepared by a process in which divalent manganese is oxidized, a process in which heptavalent manganese is reduced, or a process in which these two processes are combined. For example, when manganese dioxide prepared by reducing heptavalent manganese is used, preferred is manganese dioxide prepared, for example, by any one of the following processes: a process in which a permanganate compound is reduced at 20 to 100° C. in a neutral or alkaline region (Zeit. Anorg. Allg. Chem., 309, pp. 1-32, and pp. 121-150 (1961)), a process in which an aqueous solution of potassium permanganate is added to an aqueous solution of manganese sulfate (O. Mancera, G. Rosenkranz, and F. Sondheimer, J. Chem. Soc., 2189 (1953)), a process in which a permanganate is reduced with a hydrohalic acid (Japanese Patent Laid-Open No. 63-57535), a process in which a permanganate is reduced with a polycarboxylic acid or a polyhydric alcohol (Japanese Patent Laid-Open Nos. 9-24275 and 9-19637), a process in which a permanganate is reduced with hydrazine, a hydroxycarboxylic acid or a salt thereof (Japanese Patent Laid-Open No. 6-269666), a process in which manganese nitrate or manganese carbonate is pyrolyzed, and a process in which an aqueous solution of manganese sulfate is electrolytically oxidized.

The present oxide catalyst which contains, in addition to the manganese oxide as the main component, potassium and one or more elements selected from the group consisting of bismuth, vanadium and tin is prepared by adding compounds containing these elements to the above-described manganese dioxide in an aqueous system so as to mix them. The addition method may be any of impregnation, adsorption, kneading, coprecipitation and the like. For example, a target oxide catalyst containing manganese, bismuth and potassium can be obtained by mixing a solution containing bismuth oxide and a divalent manganese compound with a solution containing potassium permanganate to react with each other, and then aging it to complete the reaction, followed by subjecting the resultant slurry precipitate to solid-liquid separation with filtering and washing. Concentration of the solutions of the raw materials, temperature at the time of mixing, and temperature and time upon aging can be arbitrarily selected for the purpose of controlling the crystal form and the specific surface area of the catalyst as well as the contents of potassium and one or more elements selected from the group consisting of bismuth, vanadium and tin. As a source for divalent manganese used in the above-described catalyst preparation, water-soluble salts are selected, and sulfates are particularly preferable among these salts. As a source for heptavalent manganese, water-soluble salts are selected, and potassium permanganate is particularly preferable among these salts. The potassium permanganate can also be used as an alkali metal source. As a source for bismuth, water-soluble salts such as bismuth sulfate and bismuth nitrate may be used, but bismuth oxide is most preferable. As a source for vanadium, water-soluble salts such as vanadium sulfate and vanadium chloride are selected, and vanadium sulfate is particularly preferable. As a source for tin, water-soluble salts such as tin sulfate and tin chloride are selected, and tin sulfate is particularly preferable.

For the purpose of obtaining a composite oxide catalyst for cyanhydrin hydration which satisfies the atomic ratios shown in the formula (I), molar ratio between potassium permanganate and a divalent manganese compound is set to 1 to 5 and preferably 1.2 to 3, and molar ratio between potassium permanganate and a bismuth compound is 0.002 to 0.6 and preferably 0.002 to 0.4. The mixed catalyst composed of the metal oxides prepared in such mixing ratios can be a catalyst for cyanhydrin hydration with a high reaction yield and a high selectivity.

$$Mn_aK_bBi_cO_d \qquad (1)$$

wherein with the proviso of a=1, b is 0.005 to 0.15, c is 0.001 to 0.1, and d is an atomic ratio of oxygen required for satisfying the valencies of the above-described respective elements.

By separating the thus produced precipitate slurry with a solid-liquid separation means such as filtration, a cake-like hydrous catalyst can be obtained. If necessary, the cake-like hydrous catalyst resulting from the solid-liquid separation may also be washed with water in order to remove mother liquor attached thereto. Water content of the catalyst cake which has been separated and obtained as described above containing a manganese oxide as a main component, potassium and one or more elements selected from the group consisting of bismuth, vanadium and tin, is usually 300 to 150 wt % (based on dry weight). The sentence "based on dry weight" referred to herein means the weight of the above catalyst cake heated to dryness at 120° C. until a constant weight is reached.

In the present invention, the hydrous cake which has been subjected to solid-liquid separation such as filtration and other means is extrusion molded into an arbitrary shape such as a ring, a cylindrical column, a circular cylinder and a star shape by use of an ordinary extrusion-granulating machine well-known to those skilled in the art.

The extrusion molded product thus obtained is first subjected to a predrying at a drying temperature of 20 to 50° C. at an average drying rate of 2 to 10 wt %/hr, preferably 4 to 8 wt %/hr (based on dry weight) until the water content reaches 100 wt % (based on dry weight) at the maximum. Various techniques are possible for the purpose of attaining the above-described predrying conditions; as an example, the drying rate can be easily controlled by placing the catalyst in a drying chamber in which a desired temperature is maintained, and gas is sufficiently circulated whilst a humidity-controlled gas is introduced into the drying chamber at a certain flow rate so that moisture-containing gas is discharged outside the chamber at the same flow rate. As the gas introduced into the chamber, any gas can be used as long as the gas does not react with the catalyst or does not degrade the catalyst; however, in view of economic efficiency, nitrogen or air is preferable. When the drying rate is too fast as compared to that in the above-described conditions, catalytic activity is not affected, but degradation of catalyst strength is caused and the catalyst becomes unsuitable for industrial application. On the other hand, when the drying rate is too slow, no problem is raised in the catalyst strength, but there is an adverse effect on the catalytic activity. When macropore distribution of a catalyst that was adversely affected in activity due to the too slow drying rate in the predrying is measured, it was found that the macropore distribution has a maximum value in a range of less than 400 Å in pore diameter. Presumably, the macropores of the catalyst become so small as to inhibit diffusion of substances, and thus the catalytic activity is adversely affected. In addition to those as exemplified above, air drying, a ventilation dryer or a fluidized dryer can be used for predrying, and the present invention does not impose any limitation thereon.

The main drying to be carried out successively is carried out under the condition of a drying temperature of 100 to 200° C., preferably 110 to 130° C. In this step, the drying is carried out until the water content reaches 15 wt % (based on dry weight) at the maximum. When the drying temperature of the main drying step is too low, the maximum of the macropore distribution appears in less than 400 Å of pore diameter and the catalytic activity is found to be degraded in the same manner as the above-described catalyst obtained with a too slow predrying rate. On the other hand, when the drying temperature is too high, the catalytic activity is not affected, but the catalyst is finished to be a bulky catalyst, and consequently the filling amount of the catalyst per the volume of the reaction vessel becomes small to be disadvantageous for equipment efficiency. Various forms of dryers would be used for the main drying, and any dryer can be used as long as the dryer achieves the targeted degree of dryness.

The physical strength of the catalyst is improved by adopting such a drying technique in which the drying of the obtained hydrous cake is carried out in at least two separate stages, namely, the predrying and the main drying. For example, according to measurement of catalyst strength based on the crushing strength test with a crushing strength measuring machine RCT-500N-E manufactured by Toyo Seiki, a conventional method employing one stage drying at a fast drying rate from the beginning gives a crushing strength of 4.4 to 4.8 kg/cm, but the present method which requires the drying to be first carried out by the step of drying at a slow rate improves the crushing strength to 5.8 to 6.0 kg/cm.

In the present invention, the molded product which has been dried in the two separate stages as described above is used for hydration reaction of cyanhydrin in a form of fixed bed or suspended bed to perform batch-wise or continuous flow reaction. Cyanhydrins as the raw material are easily produced from various carbonyl group-containing compounds and hydrogen cyanide in the presence of a basic catalyst. Specific examples of cyanhydrins include acetone cyanhydrin and lactonitrile. The hydration reaction using the catalyst of the present invention is usually carried out in a system containing excessive water. Specifically, the proportion of cyanhydrin in a raw material solution is 5 to 80 wt %, preferably 20 to 60 wt %, and hence the proportion of water is 20 to 95 wt %, preferably 40 to 80 wt %. The reaction temperature falls in a range from 10 to 100° C., preferably from 20 to 90° C. When the temperature is lower than this range, the reaction rate becomes low; on the other hand, when the temperature is higher than this range, by-products due to decomposition of cyanhydrin are increased, unfavorably.

As described above, the use of the catalyst excellent in both strength and activity, produced by the method of the present invention, enables the hydration of cyanhydrins to be carried out stably for a long time. For example, in the case of hydration reaction of acetone cyanhydrin in a trickle-type reaction system, a molded catalyst before the present improvement undergoes a remarkable increase in pressure loss due to pulverization of the catalyst after a reaction period of approximately 6 months; however, the catalyst after the present improvement is inhibited from pulverization and enables one year or more of operation.

EXAMPLES

Hereinafter, the present invention is described more specifically by way of Examples and Comparative Examples, but the scope of the present invention is not limited to these Examples.

(Preparation of Catalyst)

Examples 1 and 2 and Comparative Examples 1 to 5

1. Preparation of Catalyst

To a solution prepared by dissolving 62.92 g (0.398 mol) of potassium permanganate in 220 ml of water, a solution prepared by dissolving 54.43 g (0.322 mol) of manganese sulfate monohydrate in 215 ml of water and further mixing therewith 99.54 g (0.964 mol) of concentrated sulfuric acid was rapidly added at 75° C. under stirring. The resultant mixture was continuously stirred at 70° C. for 2 hours, then further stirred at 90° C. for 4 hours for aging, and then rapidly supplemented with a solution prepared by suspending 1.90 g (0.007 mol) of bismuth(III) oxide in 440 ml of water. The resultant mixture was stirred for 30 minutes at room temperature, and then the obtained precipitate was filtered off, and washed four times with 200 ml of water to yield a precipitated cake. The obtained cake was molded with an extrusion molding machine (cylinder diameter: 35 mmΦ, nozzle diameter 1.5 mmΦ×24 holes, open area percentage: 4.4%, hydraulic type), subjected to a predrying with a ventilation dryer under a specified condition, and then subjected to a main drying under a specified condition to yield approximately 60 g of molded catalysts having a shape of 1.0 mmϕ×3 to 7 mm. The contents of metal components in the catalysts thus obtained were measured; consequently, the catalysts all had a ratio of bismuth/potassium/manganese=0.01/0.09/1.0 (atomic ratio). The physical properties of the respective catalysts are shown in Table 1.

2. Measurements of Crushing Strength and Packing Density

Crushing strength of the respective catalysts different in drying conditions from each other was measured with a crushing strength measuring machine RCT-500N-E manufactured by Toyo Seiki Seisaku-Sho, Ltd., using 5 to 6 mm long molded catalysts prepared as described above. The crushing strength of the respective molded catalysts was evaluated on the basis of the averaged value of 20 runs of measurements. Packing density of the respective catalysts was measured by visually observing the volume of approximately 50 g of the catalyst packed in a 200-ml graduated cylinder. The packing density was the averaged value of 5 runs of measurements without tapping in packing. The results are shown in Table 1.

TABLE 1

| Example | Predrying condition | Water content after predrying (%) (based on dry weight) | Predrying rate (%/hr)[1] | Main drying condition | Water content after main drying (%) (based on dry weight) | Crushing strength (kg/cm) | Packing density (g/ml) |
|---|---|---|---|---|---|---|---|
| Example 1 | 30° C. 24 hr | 98 | 4.9 | 110° C. 8 hr | 3.9 | 6.0 | 0.52 |
| Example 2 | 30° C. 24 hr | 40 | 7.3 | 110° C. 8 hr | 3.0 | 5.8 | 0.52 |
| Comparative Example 1 | 30° C. 72 hr | 82 | 1.9 | 110° C. 8 hr | 4.6 | 6.1 | 0.53 |
| Comparative Example 2 | 30° C. 24 hr | 98 | 4.9 | 60° C. 8 hr | 15.8 | 7.7 | 0.54 |
| Comparative Example 3 | 30° C. 24 hr | 98 | 4.9 | 200° C. 8 hr | 0.8 | 6.6 | 0.46 |
| Comparative Example 4 | Without predrying | * | * | 110° C. 8 hr | 3.5 | 4.8 | 0.41 |
| Comparative Example 5 | 60° C. 8 hr | 90 | 15.7 | 110° C. 8 hr | 4.2 | 4.0 | 0.46 |

[1]To control the predrying rate, flow rate of air was regulated.

3. Pore Volume, Pore Area and Pore Diameter Peak

They were measured with a mercury porosimeter (Autopore III from Shimadzu Corp.). The results are shown in Table 2.

4. Measurement of Hydration Performance for Acetone Cyanhydrin

Catalyst performance for hydration of cyanhydrin was evaluated by measuring conversion rate of acetone cyanhydrin and selectivity of produced 2-hydroxyisobutyric acid amide with passage of days. Specifically, 3 g of the respective catalyst prepared by means of the above-described method was filled in a glass reaction tube with an inner diameter of about 10 mmφ equipped with a jacket, then warm water at 60° C. was allowed to flow through the jacket, and thereafter a raw material solution prepared by mixing 40 wt % of acetone cyanhydrin, 10 wt % of acetone and 50 wt % of water together was allowed to flow through the reaction tube at a flow rate of 15 g/hr. The liquid flowing out of the reactor was analyzed with a high performance liquid chromatography at elapsed times of one day, seven days and 14 days from the start of the reaction to obtain the conversion rate of acetone cyanhydrin and the yield of 2-hydroxyisobutyric acid amide. The results are shown in Table 2.

The invention claimed is:

1. A process for producing a catalyst for cyanhydrin hydration, the catalyst comprising a manganese oxide as a main component, potassium, and one or more elements selected from the group consisting of bismuth, vanadium and tin, which comprises:

mixing the manganese oxide or a manganese-containing precursor thereof and compounds containing potassium and one or more of said elements together in an aqueous system;

subjecting the resulting precipitate in a form of slurry to solid-liquid separation; and drying the resulting hydrous cake in at least two separate stages comprising a predrying and a main drying, wherein the predrying is carried out at a drying temperature of 20 to 50° C. and at an average drying rate of 2 to 10 wt%/hr (based on dry weight) until water content of the hydrous cake reaches 100 wt% (based on dry weight) at the maximum and wherein the main drying is carried out at a drying temperature of 100 to 200° C. until water content of the hydrous cake reaches 15 wt % (based on dry weight) at the maximum, whereby said catalyst is obtained.

TABLE 2

| Example | Pore volume (ml/g) | Pore area (m²/g) | Pore diameter peak (Å) | Yield of 2-hydroxyisobutyric acid amide (mol %) | | |
|---|---|---|---|---|---|---|
| | | | | After one day | After seven days | After 14 days |
| Example 1 | 0.59 | 82 | 565 | 83 | 83 | 78 |
| Example 2 | 0.52 | 81 | 478 | 65 | 82 | 77 |
| Comparative Example 1 | 0.67 | 113 | 220 | 78 | 73 | * |
| Comparative Example 2 | 0.60 | 100 | 270 | 80 | 75 | 71 |
| Comparative Example 3 | 0.65 | 85 | 419 | 86 | 81 | 75 |
| Comparative Example 4 | 0.60 | 74 | 580 | 86 | 80 | 75 |
| Comparative Example 5 | 0.56 | 73 | 522 | 85 | 81 | 75 |

2. The process for producing a catalyst for cyanhydrin hydration, according to claim 1, wherein the catalyst for cyanhydrin hydration is a composite oxide represented by the following formula (1):

$$Mn_aK_bBi_cO_d \quad (1)$$

wherein with the proviso of a =1, b is 0.005 to 0.15, c is 0.001 to 0.1, and d is an atomic ratio of oxygen required for satisfying the valencies of the above-described respective elements.

3. The process for producing a catalyst for cyanhydrin hydration, according to claim 2, wherein the bismuth compound used in preparation of the catalyst is bismuth oxide.

4. A catalyst for cyanhydrin hydration, produced by the process according to claim 1.

5. The catalyst for cyanhydrin hydration, according to claim 4, which has a macropore distribution the maximum value of which falls in a range of 400 Å or more in terms of pore diameter.

6. The process for producing a catalyst for cyanhydrin hydration, according to claim 1, wherein in the predrying the average drying rate of 4 to 8 wt %/hr (based on dry weight) until water content of the hydrous cake reaches 100 wt % (based on dry weight) at the maximum.

7. The process for producing a catalyst for cyanhydrin hydration, according to claim 1, wherein in the main drying the drying temperature is 110 to 130° C.

8. The process for producing a catalyst for cyanhydrin hydration, according to claim 1, wherein in the mixing manganese dioxide is mixed with the compound containing potassium, and the at least one or more of said elements.

9. The process for producing a catalyst for cyanhydrin hydration, according to claim 1, wherein the manganese-precursor thereof is a manganese salt, and in the mixing the manganese oxide or the manganese salt is mixed with the compound containing potassium, and the at least one or more of said elements.

10. The process for producing a catalyst for cyanhydrin hydration, according to claim 1, wherein the manganese-precursor thereof is a manganese salt, and in the mixing the manganese salt is mixed with the compound containing potassium, and the at least one or more of said elements.

* * * * *